(12) United States Patent
Hsu

(10) Patent No.: US 7,816,018 B2
(45) Date of Patent: Oct. 19, 2010

(54) ORGANIC ELECTROLUMINESCENT MATERIALS AND ORGANIC ELECTROLUMINESCENT DEVICE USING THE SAME

(75) Inventor: Hsiang-Lun Hsu, Shanghai (CN)

(73) Assignee: Grace Semiconductor Manufacturing Corporation, Shanghai (CN)

( * ) Notice: Subject to any disclaimer, the term of this patent is extended or adjusted under 35 U.S.C. 154(b) by 1002 days.

(21) Appl. No.: 11/602,214

(22) Filed: Nov. 21, 2006

(65) Prior Publication Data

US 2008/0118774 A1    May 22, 2008

(51) Int. Cl.
*H01L 51/54* (2006.01)
*C09K 11/06* (2006.01)

(52) U.S. Cl. ............. 428/690; 428/917; 313/504; 257/E51.044; 548/103; 548/108

(58) Field of Classification Search .............. None
See application file for complete search history.

(56) References Cited

U.S. PATENT DOCUMENTS

2007/0190359 A1 *  8/2007  Knowles et al. ............ 428/690

* cited by examiner

*Primary Examiner*—Marie R. Yamnitzky
(74) *Attorney, Agent, or Firm*—Rosenberg, Klein & Lee

(57) ABSTRACT

An organic electroluminescent material having the formula

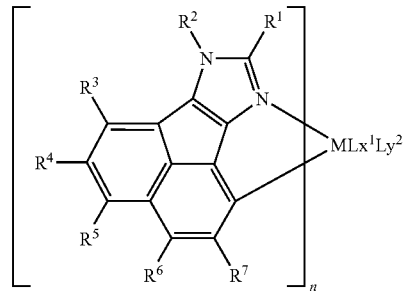

and an organic electroluminescent material used for electroluminescent devices is characterized by emission with a high luminance, high illuminant efficiency, low drive voltage, favorable color purity and high thermal steadiness. The hydrogen atom, halogen atom, cyanide group, alkyl group, alkylidene group, cycloalkane group, alkoxy group, amino group, aromatic hydroxy group, alkylaryl group as a substitutive group are used. Not only may it increase the material's glass transition temperature and inhibit the phenomenon of molecular split but also cause this organic electroluminescent device to show a high level of steadiness.

18 Claims, 3 Drawing Sheets

ORGANIC ELECTROLUMINESCENT MATERIALS AND ORGANIC ELECTROLUMINESCENT DEVICE USING THE SAME

BACKGROUND OF THE INVENTION

1. Field of the Invention

The present invention relates to an illuminant material and an illuminant device, especially as it relates to organic electroluminescent material and an organic electroluminescent material to be used for electroluminescent devices.

2. Description of the Prior Art

LCD displays are becoming more and more popular, but they still have the disadvantages of narrow angle view, slow response time for high-speed animation, high power consumption for a back light panel and are not suitable for producing a large LCD screen. In such circumstances, research on a next generation flat panel display apparatus and a planar light source illumination for an organic light-emitting diode (OLED) of a self-luminescence, wide angle view, low power consummation, simple process for manufacturing, low cost, fast response time and entire color scheme are actively conducted.

FIG. 1 shows a macromolecular light-emitting diode with single layer structure. The organic light-emitting diode 10 comprises a transparent substrate 12, a transparent anode 14, an organic electroluminescent layer 16 and a cathode 18. When DC voltage is applied to an organic light-emitting diode 10, holes are injected in the other from an anode 14. Meanwhile, electrons are injected in the other from a cathode 18. Now, owing to an external electrical field it creates a potential difference that causes carriers to drift, contact and bind from one end of an organic electroluminescent layer 16 to the other. After electronics and holes bind together, then excitons are created for exciting a luminescent molecule which emits from an organic electroluminescent layer 16. The electroluminescent molecule releases their energy as light. This luminescent molecule typically comprises an organic electroluminescent material of small molecule and macromolecular.

Many organic materials for an electroluminescent layer have already developed for a long time. In 1987, C. W. Tang and S. A. Vanslyke aime at the organic electroluminescent layer to release an organic thin film layer and the double layer structure for a hole/electron transmissive thin film layer. Lett's luminous chrominance can be dependent upon the variance of the difference in band gap between the ground-state and the excited-state of material. This is so-called the fluorescence structure. Besides the 1998, Baldo with a few people doping red phosphorescence dyes into $Alq_3$, and they discover the efficiency of energy transmission between $Alq_3$ and PtOEP almost reaches 90%. This result causes the triple-state energy transmission between $Alq_3$ and PtOEP that can be passed by an implementation of Dexter energy transmission process. It is therefore quite as important discovery for producing the high efficiency of the EL device. In 1999, Forrest, Burrow, Thompson and Baldo publish the organic electroluminescent material that is designed by metallic chelation with $Ir(ppy)_3$ fac-tris(2-phenylpyridine)iridium structure. It provides for making a green light-emitting device (Appl. Phys. Lett 74:4, 1999). Furthermore, owing to this luminous structure it emits phosphorescence, phosphorescent efficiency improvement is obtained. Over the past years, Forrest with a few people have proposed many related derivatives such as $Ir(ppy)_3$ and PtOEP, and have obtained patent applications such as U.S. Pat. Nos. 6,573,651, 6,303,238, 6,579, 632 etc. Due to $Ir(ppy)_3$ it will be far more stable than Alq3, and an organic light-emitting diode material is suitable for use in phosphorescent family. The mechanism of phosphorescent belongs to the class of the triplet state of the luminance, no matter what the probability of occurrence and the luminous efficiency are, they are all better than phosphorescent light emitting structure.

Therefore, the $Ir(ppy)_3$ derivatives devote more and more attention, and it widely uses the organic electroluminescent material and light-emitting device. On the other hand, there are also some disadvantages, such as it spends too much time for light attenuation, the severe quenching of triplet state causes components that are life limited and low color purity etc.

In order to solve the above-mentioned disadvantages of $Ir(Ppy)_3$, the present invention provides an organic electroluminescent material and an electroluminescent device to solve the above-mentioned problem.

SUMMARY OF THE INVENTION

The main object of the present invention is to provide an organic electroluminescent material, which is characterized as having a high luminance, high illuminant efficiency, and high thermal steadiness.

Another object of the present invention is to provide an organic electroluminescent material, and it is characterized as having the advantage of low drive voltage and high color purity.

In order to reach the above-mentioned goals, the present invention is to provide an organic electroluminescent material. The structure is as follows:

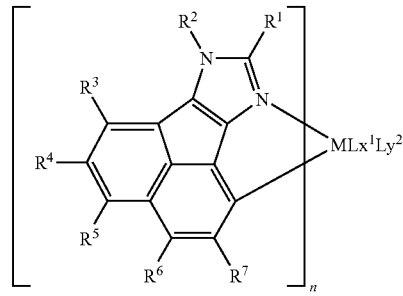

Wherein, $n=1\sim3$; $R^1$ represents a hydrogen atom or a cyanide group, an alkyl group, an alkylidene group, a cycloalkane group, an alkoxy group, an amino group or a group which is optionally chosen from the combinations; $R^2$ represents a hydrogen atom, a halogen atom, a cyanide group, an alkyl group, an alkylidene group, a cycloalkane group, an alkoxy group, an amino group, an aromatic hydroxyl group, an aromatic bi-alkyl group, or a group which is optionally chosen from the combinations; each $R^3$, $R^4$, $R^5$, $R^6$ and $R^7$ represents a hydrogen atom, a halogen atom, a cyanide group, an alkyl group, an alkylidene group, a cycloalkane group, an alkoxy group, an amino group; an aromatic hydroxy group, an aromatic bi-alkyl group, an alkylaryl group, and alkylidene group is $C_nF_{2n+1}$, alkoxy group is $OC_nF_{2n+1}$. M is Os, Ir, Ru, Rh, Pt, Pd, and $L^1$ and $L^2$ act as a monodentate or a bidentate.

When $n=2$, $x=y=1$, $L^1$ and $L^2$ act as a monodentate, M is Os, Ir, Ru or Rh; when $n=2$, $x=2$, $y=0$, $L^1$ acts as a monodentate, M is Os, Ir, Ru, Rh; when $n=2$, $x=1$, $y=0$, $L^1$ acts as bidentate, M is Os, Ir, Ru Rh; when $n=2$, $x=y=0$, M is Pt and Pd; when $n=3$, $x=y=0$, M is Os, Ir, Ru, Rh; when $n=1$, $x=y=1$, L¹ and L² act as a monodentate, M is Pt and Pd; when n=1, x=2, y=0, L¹ acts as a monodentate, M is Pt and Pd; when n=1, x=1, y=0, L¹ acts as a bidentate, M is Pt and Pd. Therefore, the organic electroluminescent material has a good performance in brightness, luminescent efficiency and thermal steadiness. Hence an organic electroluminescent material is used for an electroluminescent device and may increase its luminance, illuminant efficiency, and thermal steadiness and reduce drive voltage.

Hereafter, the other objects in accordance with the purpose of the present invention are discussed below with reference to the Figures and embodiments for explaining technical concepts and features.

DETAILED DESCRIPTION OF THE PREFERRED EMBODIMENTS

The present invention is to provide an organic electroluminescent material, and also is to provide an organic electroluminescent material is used for electroluminescent device. The overall structure of compounds is as follows:

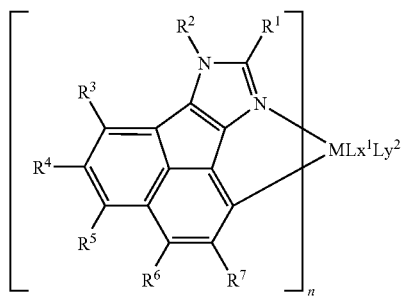
(I)

Wherein, n=1~3; $R^1$ represents a hydrogen atom or a cyanide group, an alkyl group, an alkylidene group, a cycloalkane group, an alkoxy group, an amino group or a group which is optionally chosen from the combinations; $R^2$ represents a hydrogen atom, a halogen atom, a cyanide group, an alkyl group, an alkylidene group, a cycloalkane group, an alkoxy group, an amino group, an aromatic hydroxyl group, an aromatic bi-alkyl group, or a group which is optionally chosen from the combinations; each $R^3$, $R^4$, $R^5$, $R^6$ and $R^7$ represents a hydrogen atom, a halogen atom, a cyanide group, an alkyl group, an alkylidene group, a cycloalkane group, an alkoxy group, an amino group; an aromatic hydroxy group, an aromatic bi-alkyl group, an alkylaryl group, and alkylidene group is $C_nF_{2n+1}$, alkoxy group is $OC_nF_{2n+1}$. M is Os, Ir, Ru, Rh, Pt, Pd, and L¹ and L² act as a monodentate or a bidentate.

When n=2, x=y=1, L¹ and L² act as a monodentate, M is Os, Ir, Ru, Rh; when n=2, x=2, y=0, L¹ acts as a monodentate, M is Os, Ir, Ru, Rh; when n=2, x=1, y=0, L¹ acts as a bidentate, M is Os, Ir, Ru, Rh; when n=2, x=y=0, M is Pt and Pd; when n=3, x=y=0, M is Os, Ir, Ru, Rh; when n=1, x=y=1, L¹ and L² act as a monodentate, M is Pt and Pd; when n=1, x=2, y=0, L¹ acts as a monodentate, M is Pt and Pd; when n=1, x=1, y=0, L¹ acts as a bidentate, M=Pt and Pd.

As a view from above, the present invention relates to a structure which has various embodiments. For example, n=2, x=y=1, L¹ and L² act as a monodentate. The organic electroluminescent materials according to the present invention are shown in the following various embodiments (1-a)~(1-j):

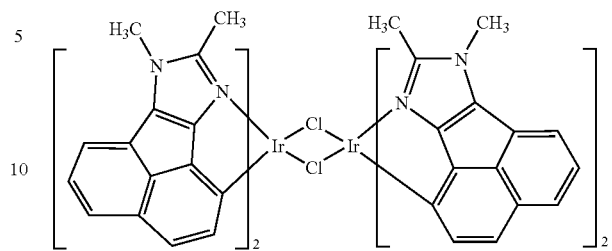
(1-a)

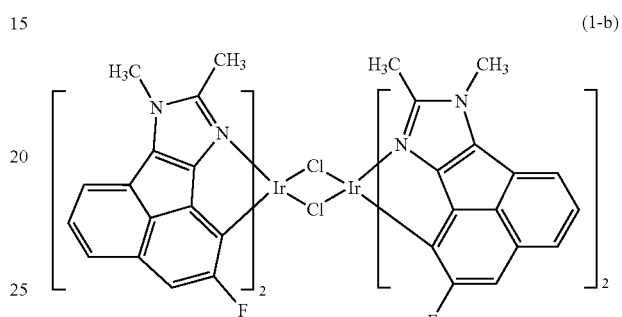
(1-b)

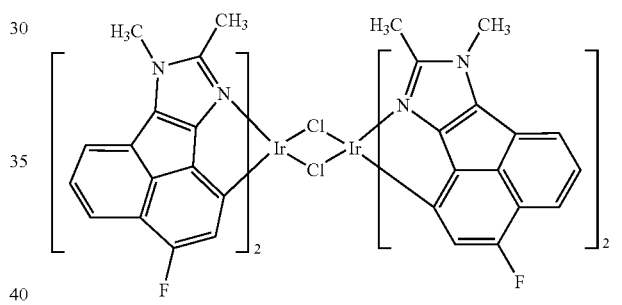
(1-c)

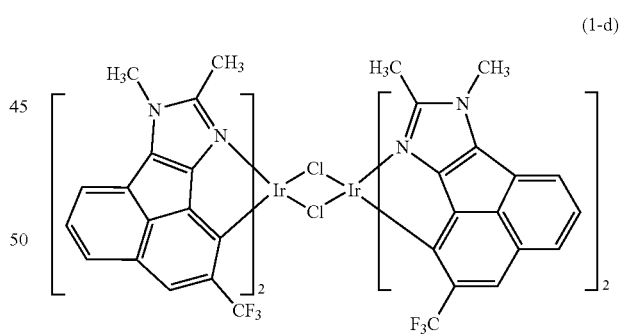
(1-d)

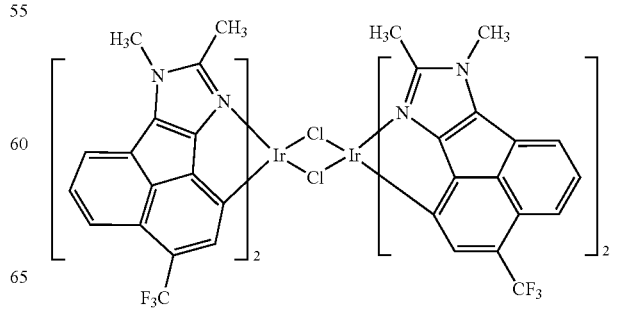
(1-e)

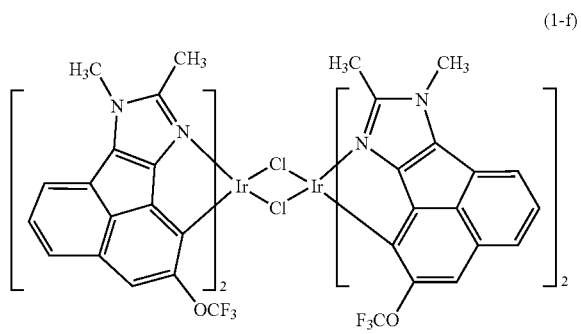
(1-f)
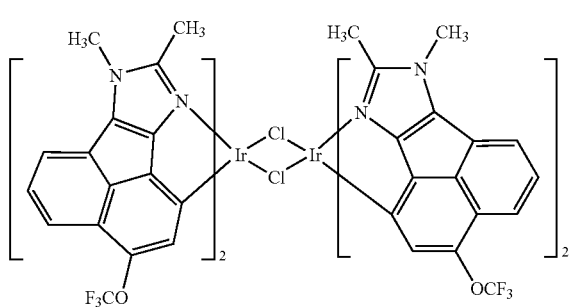
(1-g)
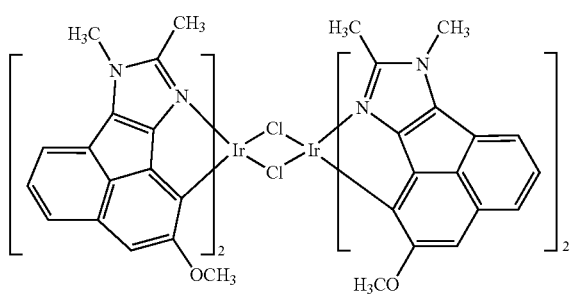
(1-h)
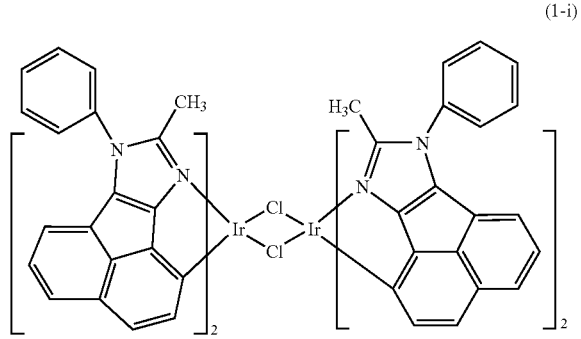
(1-i)
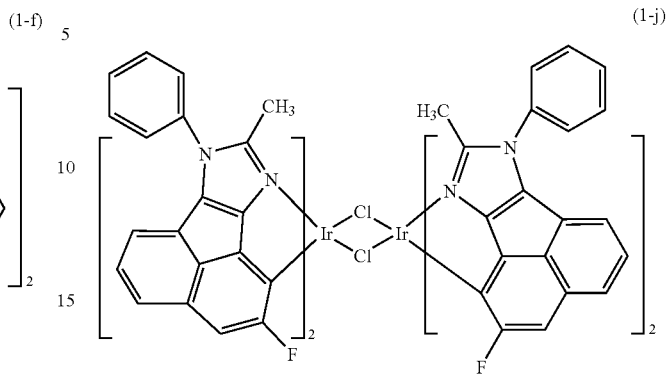
(1-j)
For example, n=3, x=0, y=0, $L^1$ and $L^2$ act as a monodentate, The luminescent materials according to the present invention are shown in the following various embodiments (2-a)~(2-j):
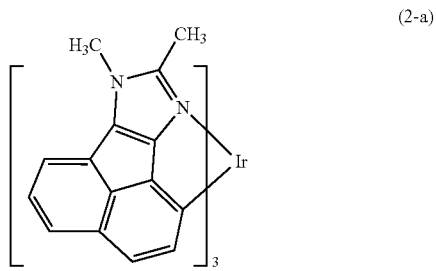
(2-a)
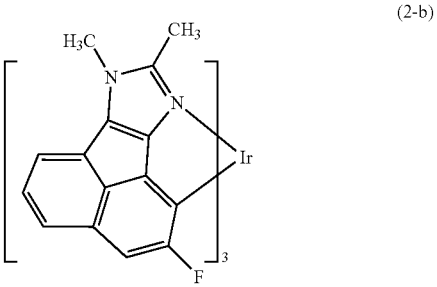
(2-b)
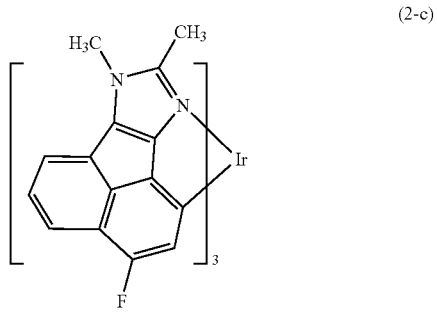
(2-c)

(2-d)
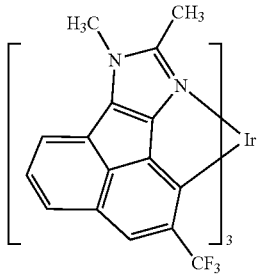
(2-e)
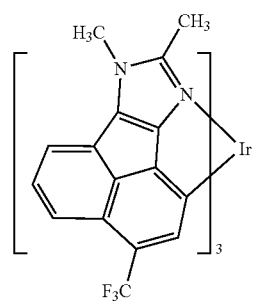
(2-f)
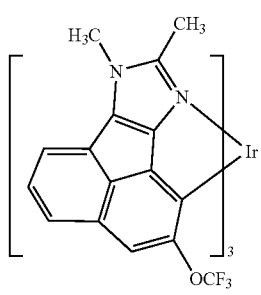
(2-g)
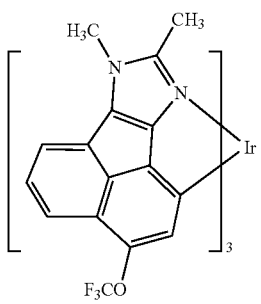
(2-h)
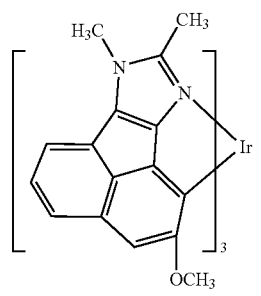
(2-i)
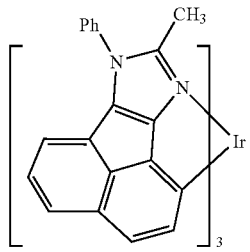
(2-j)
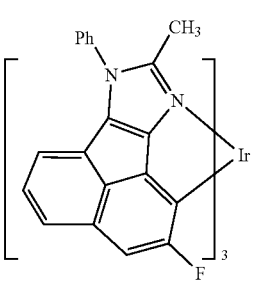
For example, n=2, x=1, y=0, $L^1$ acts as a bidentate, or n=2, x=y=1, $L^1$ and $L^2$ act as a monodentate. The luminescent materials according to the present invention are shown in the following various embodiments (3-a)~(3-l):
(3-a)
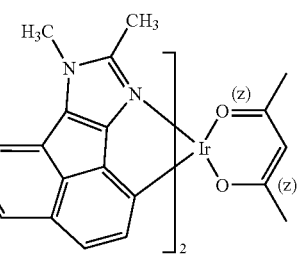
(3-b)
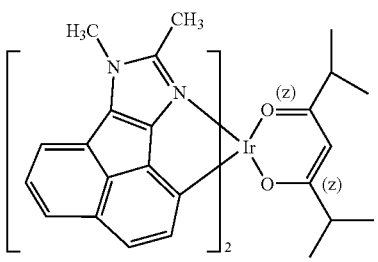
(3-c)
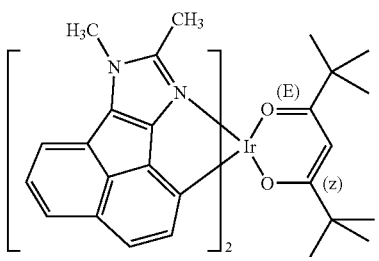

-continued
(3-d) 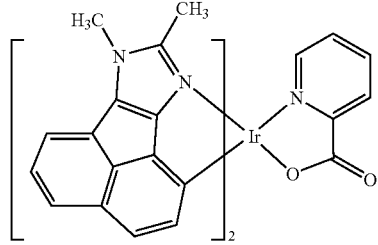
(3-e) 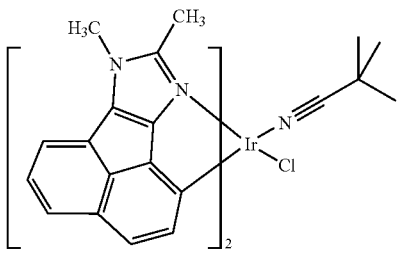
(3-f) 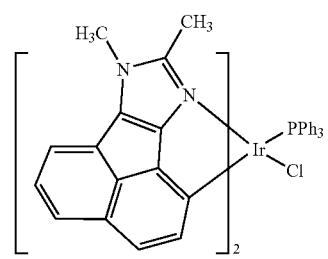
(3-g) 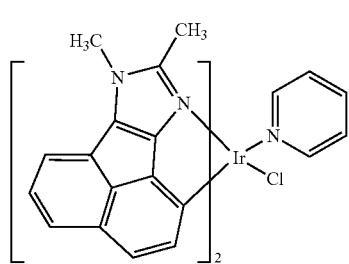
(3-h) 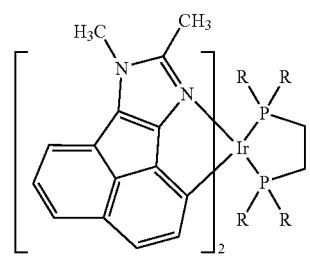
(3-i) 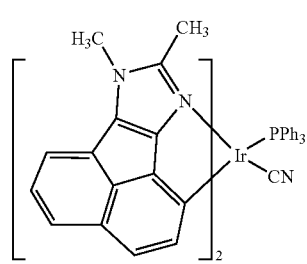
-continued
(3-j)
(3-k)
(3-l)
For example, n=1, x=y=1, $L^1$ and $L^2$ act as a monodentate, M=Pt, or n=1, x=2, y=0, $L^1$ acts as a monodentate, M is Pt and Pd, or n=1, x=1, y=0, $L^1$ acts a bidentate, M is Pt. The luminescent materials according to the present invention are shown in the following various embodiments (4-a)~(4-f):
(4-a) 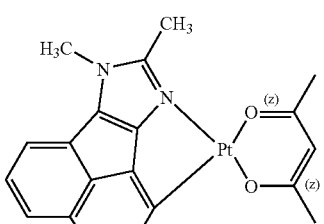
(4-b) 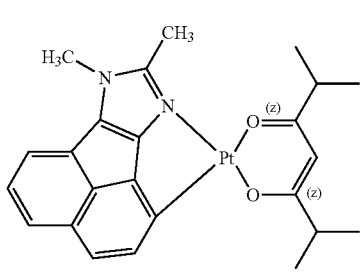

-continued (4-c)
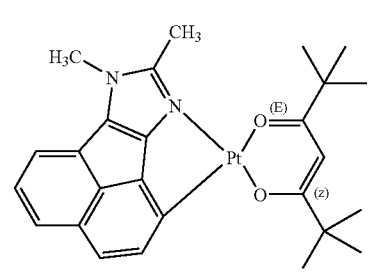

(4-d)
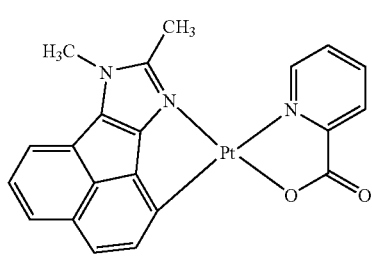

(4-e)
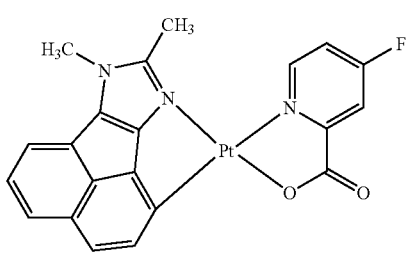

(4-f)
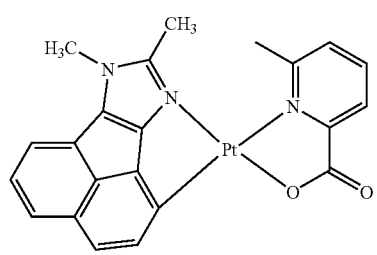

In order to describe the organic electroluminescent material and the compounded process for the organic electroluminescent material in detail, the methods according to the present invention are shown in the following various embodiments (1-a), (2-a)and (3-a).

First, 100 ml sized two-neck round-bottom flask is used to add 1.82 gm (0.01 mole) of 7,8 acenaphthrenequinone, 2.37 gm (0.03 mole) of ammonium bicarbonate, 1.45 gm (0.011 mole) of acetaldehyde and 30 ml of acetic acid under nitrogen, then heat, stir and recirculate for 12 hours under 100° C., and then hold still until it cools back down to room temperature. It may have a faint yellow solid to separate out, and thus filter out a solid from the reactive liquid. Finally, after vacuum drying is used to dry out the solid, a compound (A) of 1.96 gm (9.5 mmole) crystallizes out. The absorption rate is 95 percent; the reactive formula is represented by the following formula (II).

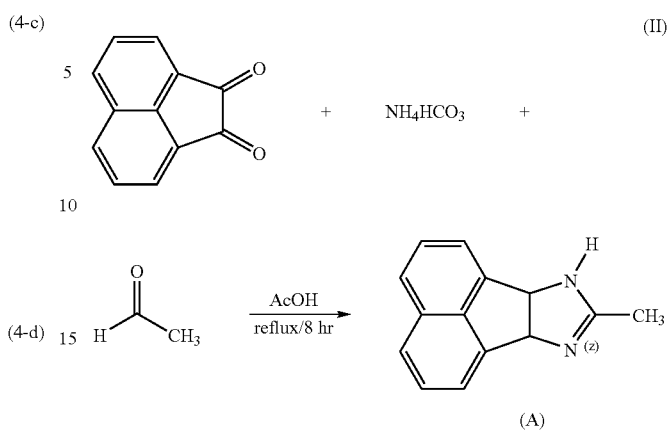

After that, take 1.50 gm of compound (A) (7.3 mmole) to add 0.21 gm (8.8 mmole) of sodium hydride into 30 ml of tetrahydrofuran and then stir under room temperature for 2 hours, then add 1.25 gm (8.8 mmole) of methyl iodide, and then heat and recirculates for 6 hours, then hold it still until it cools back down to room temperature. Finally, after vacuum drying is used to dry out the solid, a compound (B) of 1.52 gm (6.9 mmole) crystallizes out. The absorption rate is 95 percent; the reactive formula is represented by the following formula (III).

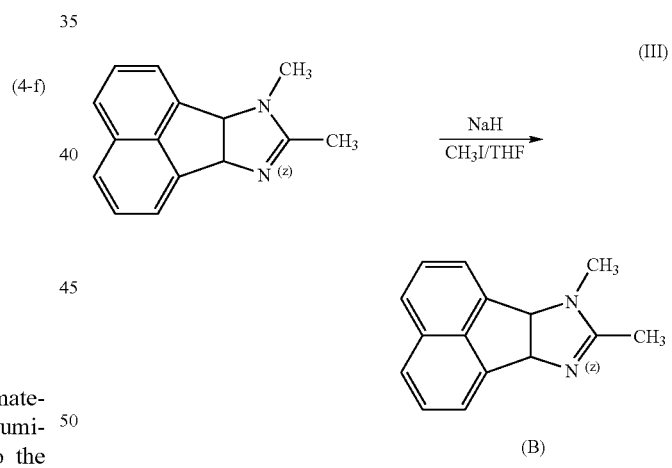

After the compound (B) is obtained, the above-mentioned compounds (1-a), (2-a), (3-a) represented by the following steps can be obtained. First, 100 ml sized of two-neck round-bottom flask is used to add 1.52 gm (6.9 mmole) of compound (B), 0.81 gm (2.3 mmole) of $IrCl_3 \cdot 3H_2O$, the ratio 3:1 of 2-ethoxyethanol and water as a solvent, then heat, stir and recirculate for 24 hours, and then hold it still until it cools back down to room temperature. It may have a solid to separate out. Finally, solid of 0.83 gm (0.8 mmole) dries out after the solvent extraction is used by vacuum pump. The absorption rate is 70 percent, this product is the above-mentioned compound (1-a), the reactive formula is represented by the following formula (IV).

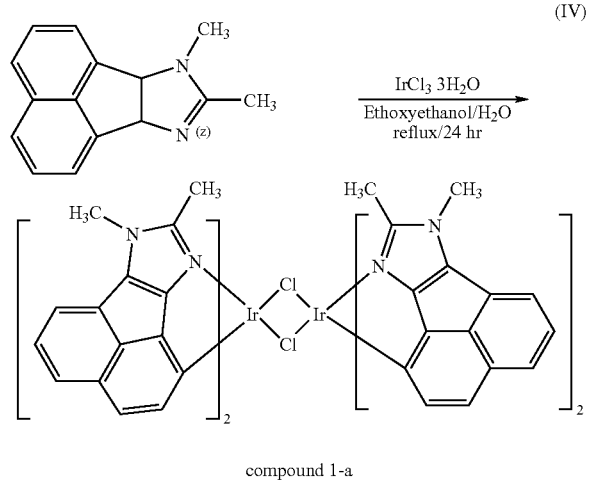

compound 1-a

Take 100 ml sized two-neck round-bottom flask to add 1.11 gm (0.8 mmole) of compound (1-a), 10 equivalents of compounds (B), 4 equivalents of $CF_3COOAg$ under nitrogen, then heat and recirculate for 12-15 hours under 200° C., and then hold it still until it cools back down to room temperature. It uses a silica gel column to purify unrefined products and obtain 0.24 gm (0.28 mmole) solids. The absorption rate is 70 percent. This product is compound (2-a), the reactive formula is represented by the following formula (V).

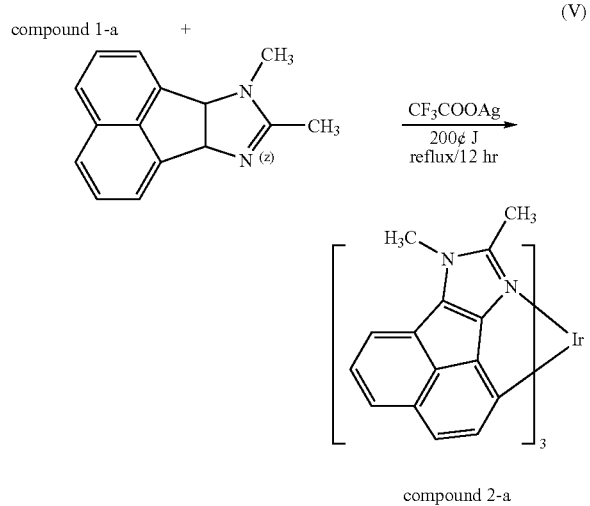

compound 2-a

The compound (2-a), which is purified by sublimation is analyzed as follows:
$^1$H-NMR ($CDCl_3$, 400 MHz) δ=7.90(d,3H); 7.80(d,6H); 7.60(m,6H); 3.63(s,9H); 2.42(s,9H).

The melting point of DSC (Differential Scanning Calorimetry) is measured at a temperature of 315° C. The glass transition temperature is measured at a temperature of 125° C. The element analysis (theoretical value) of
C %=65.13% (65.59%); H %=3.87% (3.91%); N %=9.77% (9.89%).

The analysis (theoretical value) of M=850.48(850.24).

Takes 100 ml sized two-neck round-bottom flask to add1.11 gm (0.8 mmole) of compound (1-a), 1.5 equivalents of acetyl acetones, 7 equivalents of $CF_3COOAg$, then heat and recirculate for 12-15 hours under 200° C., then hold it still until it cools back down to room temperature, and then filter out a solid from the reactive liquid, using water and hexane to clean twice then obtain unrefined products. Again use a silica gel column to purify unrefined products and obtain 0.20 gm (0.28 mmole) solids. The absorption rate is 70 percent. This product is the above-mentioned compound (3-a), the reactive formula is represented by the following formula (VI).

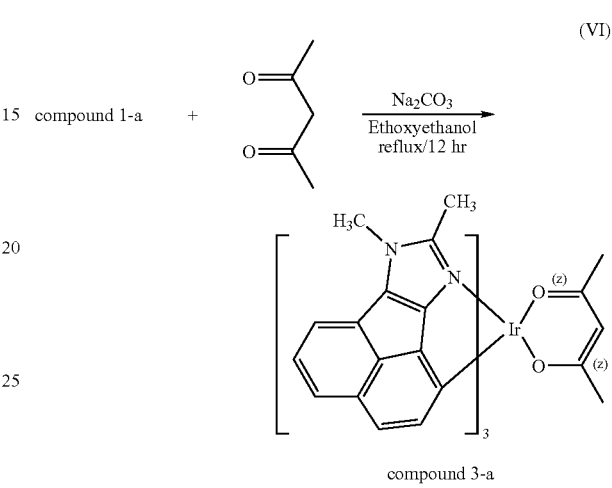

compound 3-a

The compound (3-a), which is purified by sublimation, is analyzed as follows:
$^1$H-NMR ($CDCl_3$, 400 MHz) δ=7.96 (d,2H); 7.65(d,4H); 3.63(s,6H); 6.1(m,1H);3.63(s,6H); 2.42(s,6H); 2.30(s,3H); 1.65(s,3H).

The melting point of DSC (Differential Scanning Calorimetry) is measured at a temperature of 302° C. The glass transition temperature is measured at a temperature of 125° C. The element analysis (theoretical value) of
C %=57.89% (57.60%); H %=4.06% (4.0%); N %=7.56% (7.68%) The mass analysis (theoretical value) of M=829.78 (730.19).

Embodiment 2

The above-mentioned organic electroluminescent materials according to the present invention are further to be used for an electroluminescent device. The electroluminescent device comprises a transparent substrate, a transparent anode, an organic electroluminescent device and a cathode. The transparent anode is formed on a transparent substrate, the organic electroluminescent layer is formed on a transparent anode, the cathode is formed on an organic electroluminescent layer. The transparent substrate can be a glass substrate, a plastic substrate or a flexible substrate. A plastic substrate and a flexible substrate can be a polycarbonate substrate or a polyester substrate. The transparent anode can be fabricated using known methods such as the sputtering method or the ion plating method, and it is formed on a transparent substrate. A transparent anode material can be an electric-conductive metal oxide, such as ITO, AZO, IZO. The luminescent layer comprises the above-mentioned organic electroluminescent materials. The electroluminescent material can be a doping material of the luminescent layer. The doping density may be in range between 0.01 wt % 50 wt %. The luminescent layer on a substrate comprises an arylamine compound of the aromatic hydroxyl substitutive group or an aromatic bi-alkyl substitutive group, an aromatic diamine compounds or an aromatic triamine compounds.

The glass transition temperature of the luminescent layer is higher than 100° C. The organic electroluminescent layer with each layer structure can use evaporation, spin coating, ink jet printing or printing that is provided to form on the transparent anode. An organic electroluminescent material as shown in the formula (I) in accordance with the present invention, which can be formed according to the following thin-film coating techniques, such as vacuum evaporation, molecular beam epitaxy, immersing, spin-on, casting, bar code, roll coating. The cathode can be formed using known methods such as evaporation, E-beam or sputtering, which contains electric-conductive materials such as aluminum, calcium, Al—Li Alloy, Ma-Ag Alloy or silver etc.

The manufacturing process of an electroluminescent device will now be described, with reference to the following detailed description of an illustrative embodiment. First, it uses a 100 mm×100 mm glass substrate, then deposits a 150 nm thick hafnium oxide on the glass substrate, after applying a yellow etching to form a 10 mm×10 mm luminescent pattern, carrying out the vacuum evaporation under pressures of $10^{-5}$ Pa, and then fabricated by depositing 50 nm of hole transmission material on the first layer. This hole-transmission material can be the following material:

NPB(N,N'-diphenyl-N,N'-bis-(1-naphthalenyl)-[1,1'-biphenyl]-4,4'-diamine). The structure is shown in the following figure. The deposition rate is maintained at 0.2 nm/sec.

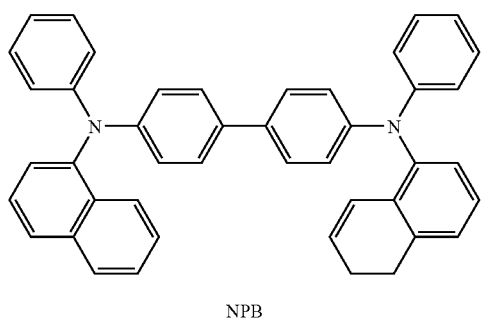

NPB

Then the second layer is deposited with an organic electroluminescent substrate material (CBP4,4'-N,N'-dicarbazole-biphenyl), in which an organic electroluminescent substrate material is around 30 nm in thickness. The deposition rate is maintained at 0.2 nm/sec.

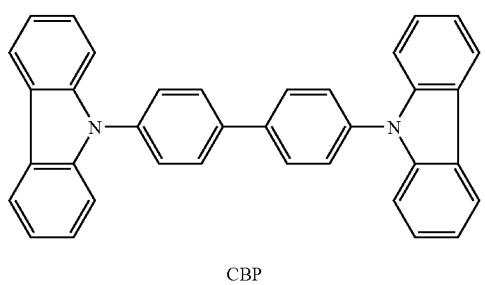

CBP

Then, the third layer is deposited with BCP(2,9-dimethyl-4,7-diphenyl-1,10-phenanthroline), and applies the above-mentioned (3-a) compounds as impurities of the luminescent layer, in which the thickness of the impurity is about 10 nm. The deposition rate is maintained at 0.2 nm/sec. And then the fourth layer is deposited with Alq3 (tris(8-quinolino)aluminum). The structure is shown in the following figure. It acts as an electronic transmission layer, in which the thickness of the electronic transmission layer is about 40 nm. The deposition rate is maintained at 0.2 nm/sec.

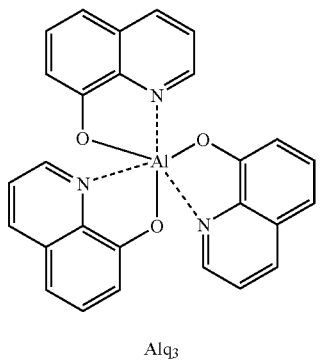

Alq3

Finally, it applies LiF(1.2 nm) and Al(150 nm) as a material to deposit on the above-mentioned electronic transmission layer to act as a cathode. Therefore, the electroluminescent device of this invention is manufactured.

It applies DC voltage to measure the illuminant characteristic for the electroluminescent device, and it to be measured by Keithly 2000. The measurement results have shown that the illuminant color is red. Besides, the EL spectrum measurement for the electroluminescent device uses the spectrometer (Otsuka Electronic Co). It also uses the photodiode array to act as a detector, in which the spectrum to be measured is shown in the FIG. 2. It shows the illuminant wavelength at 610 nm, the current-brightness-voltage measurement (I-B-V) for the electroluminescent device, shown in the FIG. 3. When the 9V is applied to the produced electroluminescent device, in which brightness, 18360 cd/m$^2$, current density, 100 mA/cm$^2$, illuminant efficiency, 8.7 lm/W and 22 cd/A, C.I.E.=(0.61,0.36) can be obtained.

The following structure is provided for comparing an organic electroluminescent material with a conventional organic electroluminescent material, and the structure is represented by the following formula VII:

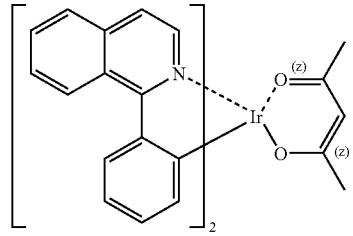

(VII)

Luminescent materials for an electroluminescent device are compounds according to the present invention represented by the following general formula VII, as shown in FIG. 3. When the 9V of voltage is applied to the produced electroluminescent device, in which brightness, 16660 cd/m², current density, 170 mA/cm², illuminant efficiency, 6.3 lm/W and 18.5 cd/A, C.I.E.=(0.63, 0.39) are obtained.

Another conventional organic electroluminescent material, the structure is represented by the following general formula VIII:

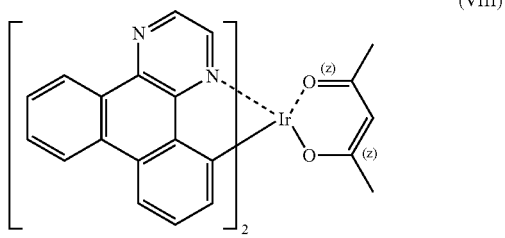

(VIII)

Luminescent materials for an electroluminescent device are compounds according to the present invention represented by the following general formula VIII, as shown in FIG. 3. When the 9 v is applied to the produced electroluminescent device, in which brightness, 12550 cd/m², current density, 125 mA/cm², illuminant efficiency, 5.3 lm/W and 15.4 cd/A, C.I.E.=(0.62, 0.36) are obtained.

Luminescent materials for an electroluminescent device are compounds (2-a) according to the present invention. When the 9 v is applied to the produced electroluminescent device, in which brightness, 1550 cd/m², current density, 15 mA/cm², illuminant efficiency, 1.3 lm/W and 3.8 cd/A, C.I.E.=(0.60, 0.39) are obtained.

It may clearly be understood after all of the above results are compared, no matter what the maximum brightness or the illuminant efficiency is. The organic electroluminescent material that is used for electroluminescent devices is obviously better than a conventional organic electroluminescent material that is used for electroluminescent devices. Besides, the organic electroluminescent material of the present invention has higher glass transition temperature. When an organic electroluminescent material of the present invention is sublimated at low pressures and high temperatures and may not occur easily in spitting of molecule. Therefore, the organic electroluminescent material of the present invention has a favorable thermal steadiness.

In summary, the present invention relates to an organic electroluminescent material and an organic electroluminescent material used for electroluminescent devices, which are characterized by high luminance, high illuminant efficiency, low drive voltage, high color purity and high thermal steadiness.

The above described embodiments are for explaining technical concepts and features. Those skilled in the art will appreciate that with various modifications, substitution is possible, without departing from the scope of the inventions which are disclosed in the accompanying claims.

Figure 1:
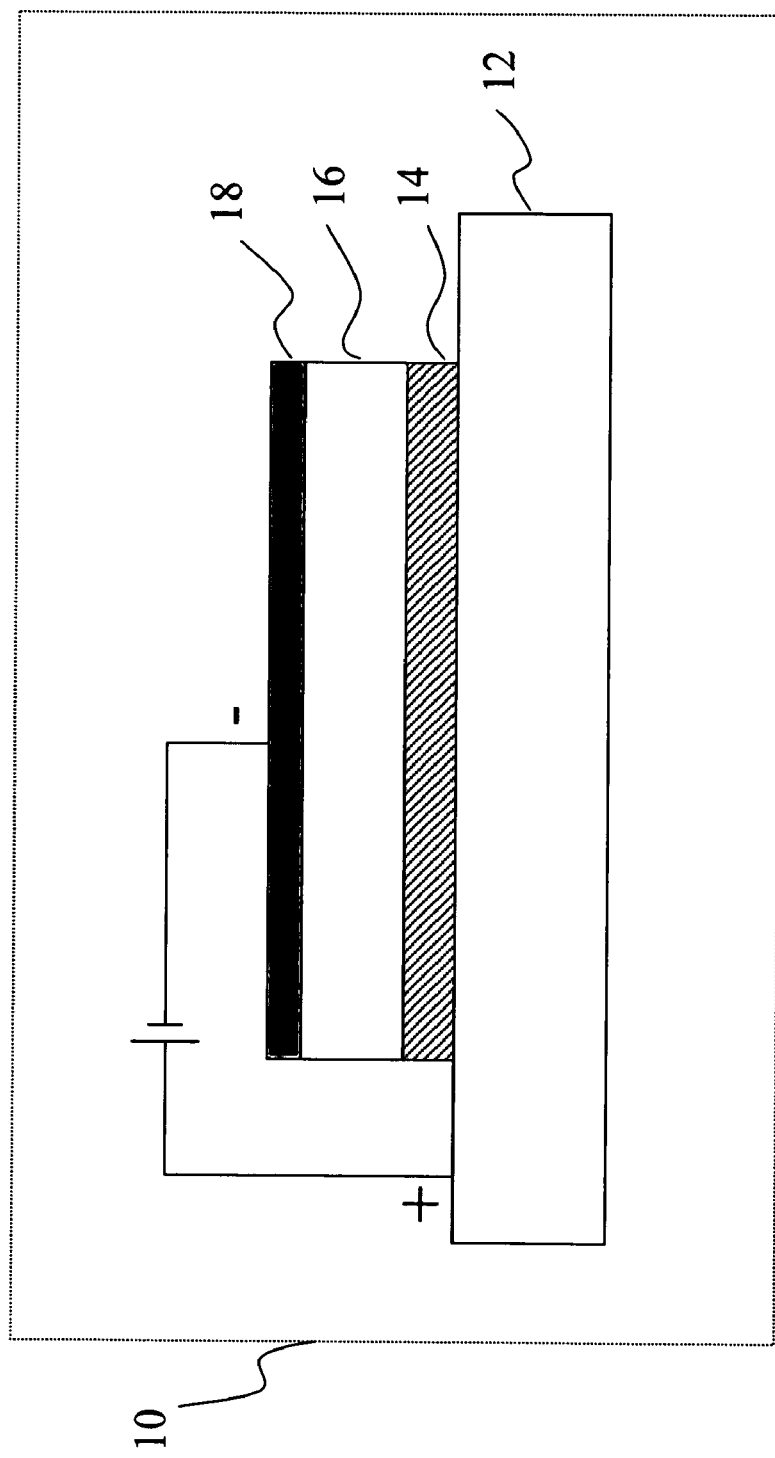
FIG. 1 is a schematic block diagram showing an example of conventional organic light-emitting diode.
Figure 2:
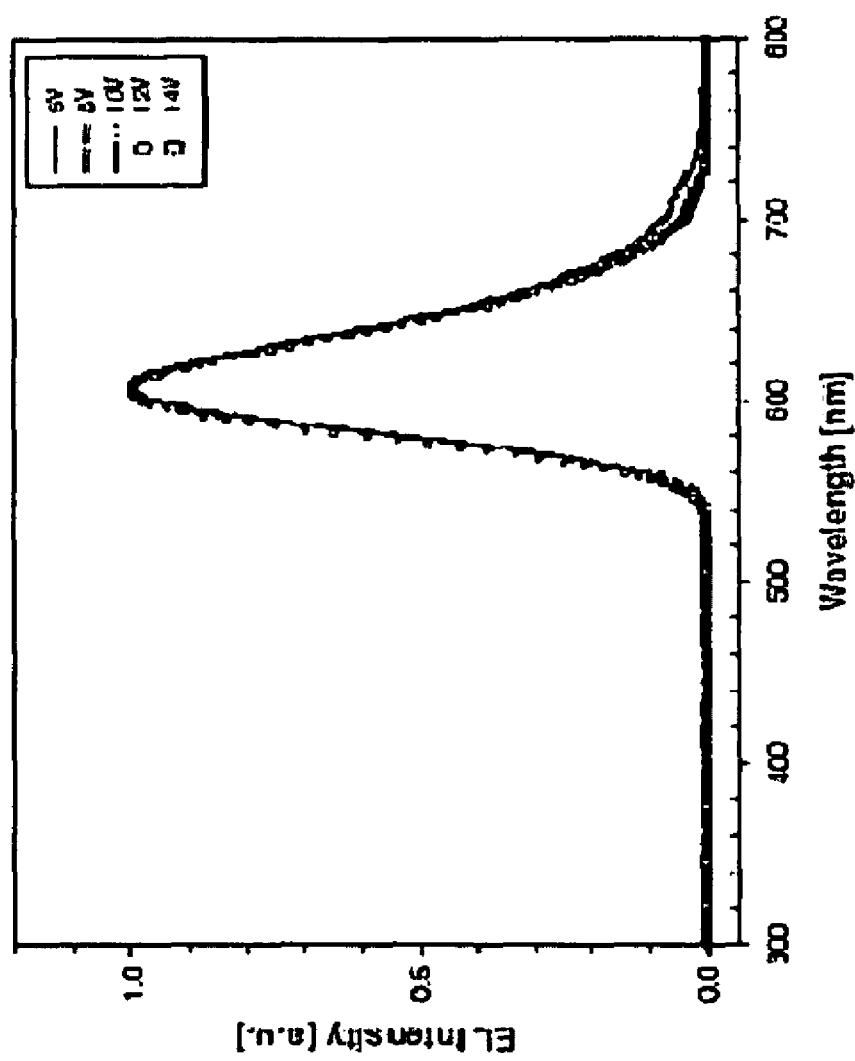
FIG. 2 is a graph showing an embodiment of the EL spectra of the electroluminescent device under various bias voltages in accordance with the present invention.
Figure 3:
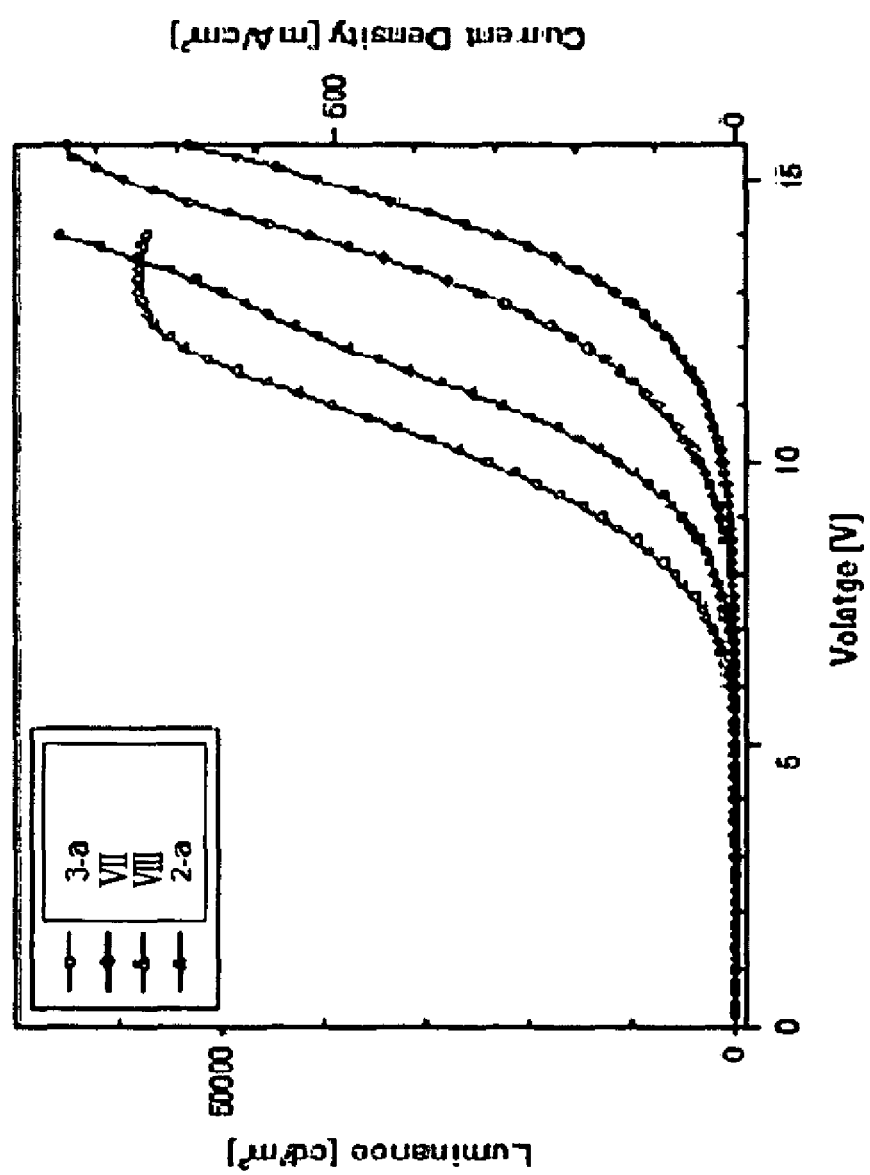
FIG. 3 is a graph showing an embodiment of the current-brightness-voltage curves of the electroluminescent device in accordance with the present invention.

What is claimed is:
1. An organic electroluminescent material, in which the structure is:

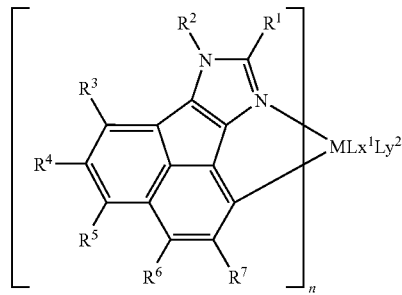

wherein, n=1-3; $R^1$ represents a hydrogen atom or a cyanide group, an alkyl group, an alkylidene group, a cycloalkane group, an alkoxy group, an amino group or a group which is optionally chosen from a combination thereof; $R^2$ represents a hydrogen atom, a halogen atom, a cyanide group, an alkyl group, an alkylidene group, a cycloalkane group, an alkoxy group, an amino group, an aromatic hydroxyl group, or a group is optionally chosen from a combination thereof; $R^3$, $R^4$, $R^5$, $R^6$ and $R^7$ represent a hydrogen atom, a halogen atom, a cyanide group, an alkyl group, an alkylidene group, a cycloalkane group, an alkoxy group, an amino group, an aromatic hydroxy group, an alkylaryl group, or a group which is optionally chosen from a combination thereof; wherein M=one of either Os, Ir, Pt, Ru, Rh or Pd; wherein $L^1$ and $L^2$ are a monodentate ligand or a bidentate ligand; wherein x=value ranging from 0-2; and wherein y=value ranging from 0-1.

2. The organic electroluminescent material according to claim 1, wherein the $R^1$ represents a hydrogen atom, a cyanide group, a substituted or unsubstituted alkyl group having 1 to 10 carbon atoms, a substituted or unsubstituted alkylidene group having 1 to 10 carbon atoms, a substituted or unsubstituted cycloalkane group having 1 to 10 carbon atoms, a substituted or unsubstituted alkoxy group having 1 to 10 carbon atoms, a substituted or unsubstituted amino group having 1 to 10 carbon atoms or a group which is optionally chosen from a combination thereof.

3. The organic electroluminescent material according to claim 1, wherein the $R^2$ represents a hydrogen atom, a halogen atom, a cyanide group, a substituted or unsubstituted alkyl group having 1 to 10 carbon atoms, a substituted or unsubstituted alkylidene group having 1 to 10 carbon atoms, a substituted or unsubstituted cycloalkane group having 1 to 10 carbon atoms, a substituted or unsubstituted alkoxy group having 1 to 10 carbon atoms, a substituted or unsubstituted amino group having 1 to 10 carbon atoms, a substituted or unsubstituted aromatic hydroxy group having 6 to 30 carbon atoms, or the group which is optionally chosen from a combination thereof.

4. The organic electroluminescent material according to claim 1, wherein the $R^3$, $R^4$, $R^5$, $R^6$ and $R^7$ represents a hydrogen atom, a halogen atom, a cyanide group, a substituted or unsubstituted alkyl group having 1 to 10 carbon atoms, a substituted or unsubstituted alkylidene group having 1 to 10 carbon atoms, a substituted or unsubstituted cycloalkane group having 1 to 10 carbon atoms, a substituted or unsubstituted alkoxy group having 1 to 10 carbon atoms, a substituted or unsubstituted amino group having 1 to 10 carbon atoms, a substituted or unsubstituted aromatic hydroxy group having 6 to 30 carbon atoms, or a group which is optionally chosen from a combination thereof.

5. The organic electroluminescent material according to claim 1, wherein the alkyl group is $C_nF_{2n+1}$.

6. The organic electroluminescent material according to claim 1, wherein the alkoxy group is $OC_nF_{2n+1}$.

7. The organic electroluminescent material according to claim 1, wherein when n=2, x=y=1, $L^1$ and $L^2$ act as a monodentate ligand, M=Os, Ir, Ru, Rh; when n=2, x=2, y=0, $L^1$ acts as a monodentate ligand, M=Os, Ir, Ru, Rh; when n=2, x=1, y=0, $L^1$ acts as a bidentate ligand, M=Os, Ir, Ru, Rh; when n=2, x=y=0, M=Pt and Pd; when n=3, x=y=0, M=Os, Ir, Ru, Rh; when n=1, x=y=1, $L^1$ and $L^2$ each act as a monodentate ligand, M=Pt and Pd; when n=1, x=2, y=0, $L^1$ acts as a bidentate ligand, M=Pt and Pd; when n=1, x=1, y=0, $L^1$ acts as a bidentate ligand, M=Pt and Pd.

8. An electroluminescent device, comprises two electrodes and an organic electroluminescent layer which is located between the two opposing electrodes, the organic electroluminescent layer comprising a material having a structure as follows:

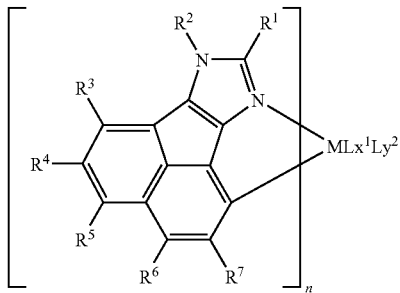

wherein, n=1-3; $R^1$ represents a hydrogen atom or a cyanide group, an alkyl group, an alkylidene group, a cycloalkane group, an alkoxy group, an amino group or a group which is optionally chosen from a combination thereof; $R^2$ represents a hydrogen atom, a halogen atom, a cyanide group, an alkyl group, an alkylidene group, a cycloalkane group, an alkoxy group, an amino group, an aromatic hydroxyl group, or a group which is optionally chosen from a combination thereof; $R^3$, $R^4$, $R^5$, $R^6$ and $R^7$ represent a hydrogen atom, a halogen atom, a cyanide group, an alkyl group, an alkylidene group, a cycloalkane group, an alkoxy group, an amino group, an aromatic hydroxy group, an alkylaryl group, or a group which is optionally chosen from a combination thereof; wherein M=one of either Os, Ir, Pt, Ru, Rh or Pd; wherein $L^1$ and $L^2$ are a monodentate ligand or a bidentate ligand; wherein x=value ranging from 0-2; and wherein y=value ranging from 0-1.

9. The electroluminescent device according to claim 8, wherein the $R^1$ represents a hydrogen atom, a cyanide group, a substituted or unsubstituted alkyl group having 1 to 10 carbon atoms, a substituted or unsubstituted alkylidene group having 1 to 10 carbon atoms, a substituted or unsubstituted cycloalkane group having 1 to 10 carbon atoms, a substituted or unsubstituted alkoxy group having 1 to 10 carbon atoms, a substituted or unsubstituted amino group having 1 to 10 carbon atoms or a group which is optionally chosen from a combination thereof.

10. The electroluminescent device according to claim 8, wherein the $R^2$ represents a hydrogen atom, a halogen atom, a cyanide group, a substituted or unsubstituted alkyl group having 1 to 10 carbon atoms, a substituted or unsubstituted alkylidene having 1 to 10 carbon atoms, a substituted or unsubstituted cycloalkane group having 1 to 10 carbon atoms, a substituted or unsubstituted alkoxy group having 1 to 10 carbon atoms, a substituted or unsubstituted amino group having 1 to 10 carbon atoms, a substituted or unsubstituted aromatic hydroxy group having 6 to 30 carbon atoms, or a group which is optionally chosen from a combination thereof.

11. The electroluminescent device according to claim 8, wherein the $R^3$, $R^4$, $R^5$, $R^6$ and $R^7$ represents a hydrogen atom, a halogen atom, a cyanide group, a substituted or unsubstituted alkyl group having 1 to 10 carbon atoms, a substituted or unsubstituted alkylidene having 1 to 10 carbon atoms, a substituted or unsubstituted cycloalkane group having 1 to 10 carbon atoms, a substituted or unsubstituted alkoxy group having 1 to 10 carbon atoms, a substituted or unsubstituted amino group having 1 to 10 carbon atoms, a substituted or unsubstituted aromatic hydroxy group having 6 to 30 carbon atoms, or a group which is optionally chosen from a combination thereof.

12. The electroluminescent device according to claim 8, wherein the alkyl group is $C_nF_{2n+1}$, the alkoxy group is $OC_nF_{2n+1}$.

13. The electroluminescent device according to claim 8, wherein when n=2, x=y=1, $L^1$ and $L^2$ each act as a monodentate ligand, M=Os, Ir, Ru, or Rh; when n=2, x=2, y=0, $L^1$ acts as a monodentate ligand, M=Os, Ir, Ru, or Rh; when n=2, x=1, y=0, $L^1$ acts as a bidentate ligand, M=Os, Ir, Ru, or Rh; when n=2, x=y=0, M=Pt and Pd; when n=3, x=y=0, M=Os, Ir, Ru, or Rh; when n=1, x=y=1, $L^1$ and $L^2$ each act as a monodentate ligand, M=Pt and Pd; when n=1, x=2, y=0, $L^1$ acts as a monodentate ligand, M=Pt and Pd; when n=1, x=1, y=0, $L^1$ acts as a bidentate ligand, M=Pt and Pd.

14. The electroluminescent device according to claim 8, wherein the organic electroluminescent layer includes an aromatic amine compound, an aromatic diamine compound or an aromatic triamine compound.

15. The electroluminescent device according to claim 14, wherein the aromatic amine compound has an aromatic hydroxyl substitutive group.

16. The electroluminescent device according to claim 14, wherein the aromatic diamine compound has an aromatic hydroxyl substitutive group.

17. The organic electroluminescent device according to claim 14, wherein the aromatic triamine compound has an aromatic hydroxyl substitutive group.

18. The organic electroluminescent device according to claim 9, wherein the organic electroluminescent material is a doped material of the organic electroluminescent layer, and a weight percentage is 0.1~50% by weight for the doping density of the organic electroluminescent material.

* * * * *